US008348997B2

(12) United States Patent  (10) Patent No.: US 8,348,997 B2
Thompson et al.  (45) Date of Patent: Jan. 8, 2013

(54) ONE-WAY REPLACEMENT VALVE

(75) Inventors: Dustin Thompson, Santa Rosa, CA (US); D. H. Perkins, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 922 days.

(21) Appl. No.: 12/391,372

(22) Filed: Feb. 24, 2009

(65) Prior Publication Data

US 2010/0217385 A1  Aug. 26, 2010

(51) Int. Cl.
*A61F 2/24* (2006.01)
*A61F 2/06* (2006.01)

(52) U.S. Cl. ......................................... 623/2.1; 623/1.26
(58) Field of Classification Search .................. 623/1.26, 623/2.1–2.42
See application file for complete search history.

(56) References Cited

U.S. PATENT DOCUMENTS

| | | | |
|---|---|---|---|
| 5,824,061 A | 10/1998 | Quijano et al. | |
| 5,957,949 A | 9/1999 | Leonhardt et al. | |
| 6,241,763 B1 | 6/2001 | Drasler et al. | |
| 6,299,637 B1 | 10/2001 | Shaolian et al. | |
| 6,319,281 B1 | 11/2001 | Patel | |
| 6,458,153 B1 | 10/2002 | Bailey et al. | |
| 6,562,068 B2 | 5/2003 | Drasler et al. | |
| 6,652,578 B2 | 11/2003 | Bailey et al. | |
| 6,716,241 B2 | 4/2004 | Wilder et al. | |
| 6,902,576 B2 | 6/2005 | Drasler et al. | |
| 6,951,571 B1* | 10/2005 | Srivastava | 623/1.24 |
| 6,958,076 B2 | 10/2005 | Acosta et al. | |
| 7,018,408 B2 | 3/2006 | Bailey et al. | |
| 7,331,991 B2 | 2/2008 | Kheradvar et al. | |
| 7,678,144 B2* | 3/2010 | Bailey et al. | 623/2.16 |
| 2001/0011189 A1 | 8/2001 | Drasler et al. | |
| 2001/0021872 A1 | 9/2001 | Bailey et al. | |
| 2002/0177894 A1 | 11/2002 | Acosta et al. | |
| 2003/0023300 A1 | 1/2003 | Bailey et al. | |
| 2003/0055492 A1 | 3/2003 | Shaolian et al. | |
| 2003/0130727 A1 | 7/2003 | Drasler et al. | |
| 2003/0171802 A1 | 9/2003 | Wilder et al. | |
| 2004/0024447 A1 | 2/2004 | Haverich | |
| 2004/0106976 A1 | 6/2004 | Bailey et al. | |
| 2004/0133267 A1 | 7/2004 | Lane | |
| 2004/0193253 A1 | 9/2004 | Thorpe et al. | |
| 2004/0215339 A1 | 10/2004 | Drasler et al. | |
| 2005/0096734 A1 | 5/2005 | Majercak et al. | |
| 2005/0137676 A1 | 6/2005 | Richardson et al. | |
| 2005/0137681 A1 | 6/2005 | Shoemaker et al. | |
| 2006/0167543 A1 | 7/2006 | Bailey et al. | |
| 2006/0178729 A1 | 8/2006 | Thielen et al. | |
| 2006/0178730 A1 | 8/2006 | Hill et al. | |
| 2006/0190074 A1 | 8/2006 | Hill et al. | |
| 2006/0247762 A1 | 11/2006 | Acosta et al. | |
| 2006/0282157 A1 | 12/2006 | Hill et al. | |
| 2007/0050013 A1 | 3/2007 | Gross | |
| 2007/0067021 A1 | 3/2007 | Haverkost et al. | |
| 2007/0093887 A1 | 4/2007 | Case et al. | |
| 2007/0112423 A1 | 5/2007 | Chu | |
| 2007/0129788 A1 | 6/2007 | Drasler et al. | |
| 2007/0142906 A1 | 6/2007 | Figulla et al. | |
| 2007/0265699 A1 | 11/2007 | Grewe et al. | |

* cited by examiner

*Primary Examiner* — Gary Jackson
*Assistant Examiner* — Michael Mendoza

(57) ABSTRACT

Artificial valves for use as a venous valve or a heart valve are disclosed. The valve includes a frame including a platform and a valve material coupled to the frame. The valve material is a plurality of filaments or a flap. The valve material is coupled to the frame such that in response to a force in a first direction, e.g. blood flow, the valve material extends in the direct of the force to allow blood to flow past the valve material. In absence of the force in the first direction, the valve material rests against the platform to block blood flow in a direction opposite the first direction.

28 Claims, 12 Drawing Sheets

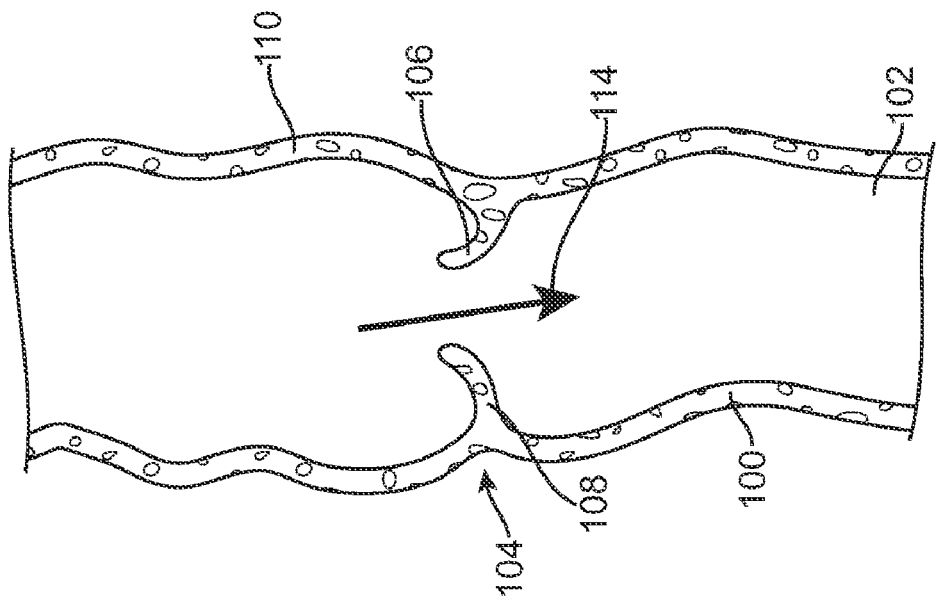
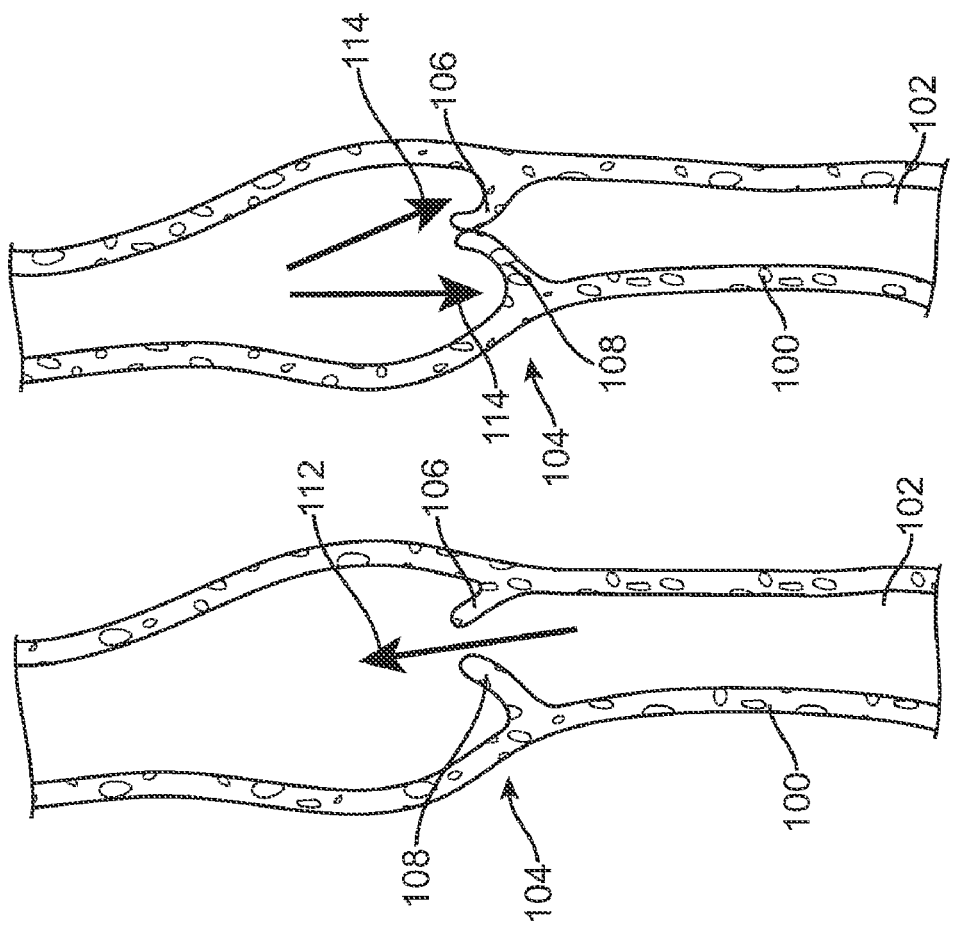
FIG. 1A  FIG. 1B  FIG. 2

ONE-WAY REPLACEMENT VALVE

FIELD OF THE INVENTION

The invention relates to one-way venous and aortic valves and methods for percutaneously delivery and deployment of such valves.

BACKGROUND

Venous valves are found within native venous vessels and are used to assist in returning blood back to the heart in an antegrade direction from all parts of the body. The venous system of the leg for example includes the deep venous system and the superficial venous system, both of which are provided with venous valves that are intended to direct blood toward the heart and prevent backflow or retrograde flow, which can lead to blood pooling or stasis in the leg. Incompetent valves can also lead to reflux of blood from the deep venous system to the superficial venous system and the formation of varicose veins. Superficial veins, which include the greater and lesser saphenous veins, have perforating branches in the femoral and popliteal regions of the leg that direct blood flow toward the deep venous system and generally have a venous valve located near the junction with the deep system. Deep veins of the leg include the anterior and posterior tibial veins, popliteal veins, femoral veins, and iliac veins. Deep veins are surrounded in part by musculature tissue that assists in generating flow due to muscle contraction during normal walking or exercising. Veins in the lower leg have a static pressure while standing of approximately 80-90 mm Hg that may reduce during exercise to 60-70 mm Hg. Despite exposure to such pressures, the valves of the leg are very flexible and can close with a pressure drop of less than one mm Hg.

FIGS. 1A-1B are schematic representations of blood flow through a healthy native valve 104 within a vein 100. Venous valve 104 controls blood flow through lumen 102 of vein 100 via leaflets 106, 108. More particularly, venous valve 104 opens to allow antegrade flow 112 through leaflets 106, 108 as shown in FIG. 1A. Venous valve 104 closes to prevent backflow or retrograde flow 114 through leaflets 106, 108 as shown in FIG. 1B.

Veins typically in the leg can become distended from prolonged exposure to excessive pressure and due to weaknesses found in the vessel wall causing the natural venous valves to become incompetent leading to retrograde blood flow in the veins. Such veins no longer function to help pump or direct the blood back to the heart during normal walking or use of the leg muscles. As a result, blood tends to pool in the lower leg and can lead to leg swelling and the formation of deep venous thrombosis and phlebitis. The formation of thrombus in the veins can further impair venous valvular function by causing valvular adherence to the venous wall with possible irreversible loss of venous function. Continued exposure of the venous system to blood pooling and swelling of the surrounding tissue can lead to postphlebitic syndrome with a propensity for open sores, infection, and may lead to possible limb amputation.

Chronic Venous Insufficiency (CVI) occurs in patients that have deep and superficial venous valves of their lower extremities (below their pelvis) that have failed or become incompetent due to congenital valvular abnormalities and/or pathophysiologic disease of their vasculature. As a result, these patients suffer from varicose veins, swelling and pain of the lower extremities, edema, hyper pigmentation, lipodermatosclerosis, and deep vein thrombosis (DVT). Such patients are at increased risk for development of soft tissue necrosis, ulcerations, pulmonary embolism, stroke, heart attack, and amputations.

FIG. 2 is a schematic representation of blood flow through an incompetent venous valve. Backflow or retrograde flow 114 leaks through venous valve 104 creating blood build-up that eventually may destroy the venous valve and cause a venous wall bulge 110. More specifically, the vessel wall of vein 100 expands into a pouch or bulge, such that the vessel has a knotted appearance when the pouch is filled with blood. The distended vessel wall area may occur on the outflow side of the valve above leaflets 106, 108 as shown in FIG. 2, and/or on the inflow side of the valve below leaflets 106, 108. After a vein segment becomes incompetent, the vessel wall dilates and fluid velocity there through decreases, which may lead to flow stasis and thrombus formation in the proximity of the venous valve.

Repair and replacement of venous valves presents a formidable problem due to the low blood flow rate found in native veins, the very thin wall structure of the venous wall and the venous valve, and the ease and frequency of which venous blood flow can be impeded or totally blocked for a period of time. Surgical reconstruction techniques used to address venous valve incompetence include venous valve bypass using a segment of vein with a competent valve, venous transposition to bypass venous blood flow through a neighboring competent valve, and valvuloplasty to repair the valve cusps. These surgical approaches may involve placement of synthetic, allograft and/or xenograft prostheses inside of or around the vein. However, such prostheses have not been devoid of problems leading to thrombus and/or valve failure due to leaflet thickening/stiffening, non-physiologic flow conditions, non-biocompatible materials and/or excessive dilation of the vessels with a subsequent decrease in blood flow rates.

The aortic valve is located at the intersection of the left ventricle of the heart and the ascending aorta. During ventricular systole, pressure rises in the left ventricle. When the pressure in the left ventricle rises above the pressure in the aorta, the aortic valve opens, allowing blood to exit the left ventricle into the aorta. When ventricular systole ends, pressure in the left ventricle rapidly drops. When the pressure in the left ventricle decreases, the aortic pressure forces the aortic valve to close.

FIGS. 3A-3B are schematic representations of blood flow through a healthy aortic valve 304 at the intersection of aorta 302 and left ventricle 306. Aortic valve 304 controls blood flow from left ventricle 306 to aorta 302. More particularly, aortic valve 304 opens to allow antegrade flow 312 through aortic valve 304 as shown in FIG. 3A. Aortic valve 304 closes to prevent backflow or retrograde flow 314 through aortic valve 304 as shown in FIG. 3B.

FIG. 5 is a schematic illustration of the junction between the aorta 302 and the heart. The aortic root 318 is the portion of the left ventricular outflow tract which supports the leaflets 334 (shown in FIG. 6) of the aortic valve 304. The aortic root 318 may be delineated by the sinotubular junction 336 distally and the bases of the valve leaflets 334 proximally. The aortic root 318 comprises the sinuses 332, the valve leaflets 334, the commissures 340, and the interleaflet triangles (not shown). The annulus 338 is the area of collagenous condensation at the point of leaflet attachment. The annulus 338 comprises a dense fibrous ring attached either directly or indirectly to the atrial or ventricular muscle fibers.

Aortic insufficiency (AI), also called aortic regurgitation, occurs when the aortic valve does not close completely when pressure in the left ventricle drops at the end of ventricular systole. Such a failure to close causes blood to flow in the reverse direction during ventricular diastole, from the aorta into the left ventricle of the heart. This means that some of the blood that was already ejected from the heart is regurgitated back into the heart. The percentage of blood that regurgitates back through the aortic valve due to AI is known as the regurgitant fraction. Since some of the blood that is ejected during systole regurgitates back into the left ventricle during diastole, there is decreased effective forward flow in AI. Aortic insufficiency causes both volume overload (elevated preload) and pressure overload (elevated afterload) of the heart.

FIG. 4 is a schematic representation of blood flow through an incompetent aortic valve 304. Backflow or antegrade flow 314 leaks through aortic valve 304 such that blood regurgitates back into the left ventricle 306.

Aortic insufficiency can be due to abnormalities of either the aortic valve or the aortic root. The surgical treatment of choice at this time is an aortic valve replacement. This is currently an open-heart procedure, requiring the individual to be placed on cardiopulmonary bypass. Further, any replacement or treatment of the aortic valve must take into account the coronary arteries. The coronary arteries (left and right) (not shown) originate from the aortic root 318 (more particularly the sinuses 332), immediately above the aortic valve. The coronary arteries supply oxygen rich blood to the muscle tissue of the heart (the myocardium). The junction of the coronary arteries with the sinuses is called the coronary ostia. The left coronary ostium 350 and right coronary ostium 352 are shown in FIGS. 9B, 13A, and 13B. The coronary ostia cannot be blocked by the replacement valve.

Similarly, pulmonary valve 310 (shown in FIGS. 3A-3B) controls blood flow from the right ventricle 311 to the main pulmonary artery 308, and eventually to the lungs. More particularly, pulmonary valve 310 opens to allow antegrade flow through pulmonary valve 310. Pulmonary valve 310 closes to prevent backflow or retrograde flow through pulmonary valve 310 back into right ventricle 311. Pulmonary valve insufficiency or regurgitation occurs when the pulmonary valve 310 does not close properly after the right ventricle 311 has finished its pumping cycle. Excess blood therefore makes the right ventricle 311 work harder than normal.

As with aortic valve insufficiency, pulmonary valve insufficiency can be due to abnormalities of either the pulmonary valve or the annulus. The surgical treatment of choice at this time is a pulmonary valve replacement. This is currently an open-heart procedure, requiring the individual to be placed on cardiopulmonary bypass.

Throughout this specification, references to a heart valve, aortic valve, or pulmonary valve can apply equally to both the aortic valve and the pulmonary valve, except where specifically noted. Thus, structures described below for the aortic valve apply equally to the pulmonary valve.

In view of the foregoing, there is still a need for methods and apparatus to restore normal venous circulation to patients suffering from venous valve insufficiency and normal circulation to the aorta to patients suffering from aortic valve insufficiency, wherein the methods and apparatus may be used in percutaneous, minimally invasive procedures.

BRIEF SUMMARY OF THE INVENTION

Embodiments hereof are directed to an artificial valve for use as a venous valve or an aortic valve. In one embodiment, the valve includes a frame including a platform and a valve material coupled to the frame. The valve material in one embodiment is a plurality of filaments. In another embodiment, the valve material is a flap. The valve material is coupled to the frame such that in response to a force in a first direction, e.g. antegrade blood flow, the valve material extends in the direction of the force to allow blood to flow past the valve material. In absence of the force in the first direction, the valve material rests against the platform to block blood flow in a direction opposite the first direction, or retrograde blood flow. The embodiment with the flap may include slits in the flap or a shape memory material in the flap.

In a method of delivering an artificial one-way valve to a target location, the one-way valve is disposed in a catheter in a compressed configuration. Percutaneous access in obtained to a vessel to reach the target location. A guidewire is tracked to the target location. The guidewire is backloaded into the catheter and the catheter is advanced over the guidewire to the target location. The valve is then released from the catheter. The valve can be delivered to the location of an incompetent venous valve or an incompetent aortic valve.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 1A-1B are schematic representations of blood flow through a healthy valve within a vein.

FIG. 2 is a schematic representation of blood flow through an incompetent valve within a vein.

DETAILED DESCRIPTION OF THE INVENTION

Specific embodiments hereof are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the deep and superficial veins of the leg, the invention may also be used in any other body passageways where it is deemed useful. Furthermore, there is no intention to be bound by any expressed or implied theory presented in the preceding technical field, background, brief summary or the following detailed description.

Figure 7:
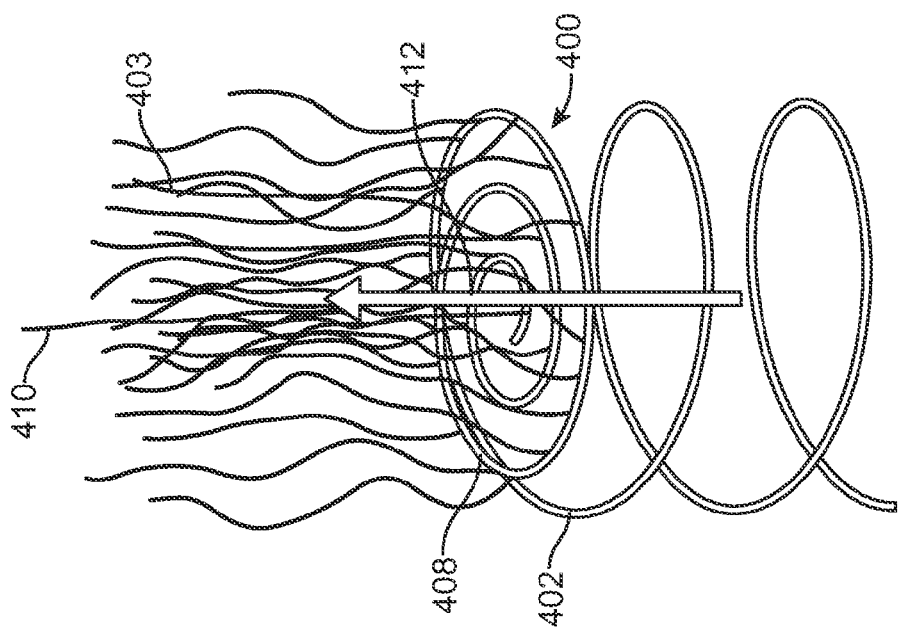
FIG. 7 is a schematic representation of a one-way valve in accordance with an embodiment hereof.

FIG. 7 is a schematic representation of one-way valve 400 in accordance with an embodiment hereof. Valve 400 includes a coil or frame 402 and a multitude of filaments 403 or ribbons coupled to the frame 402. Frame 402 is preferably formed from a shape memory material, such as a nickel-titanium alloy (Nitinol), such that frame 402 is self-expanding. It would be understood by those skilled in the art that frame 402 can be made of other materials used, for example, in stents, and may be balloon expandable. In another example, frame 402 may be made from a metal-to-metal composite with tantalum as the core material and Nitinol as the cover or tube material, such as available from Fort Wayne Metals in their DFT® wire. Such a frame material would permit enhanced visualization of frame 402 due to the tantalum core.

Figure 3A:
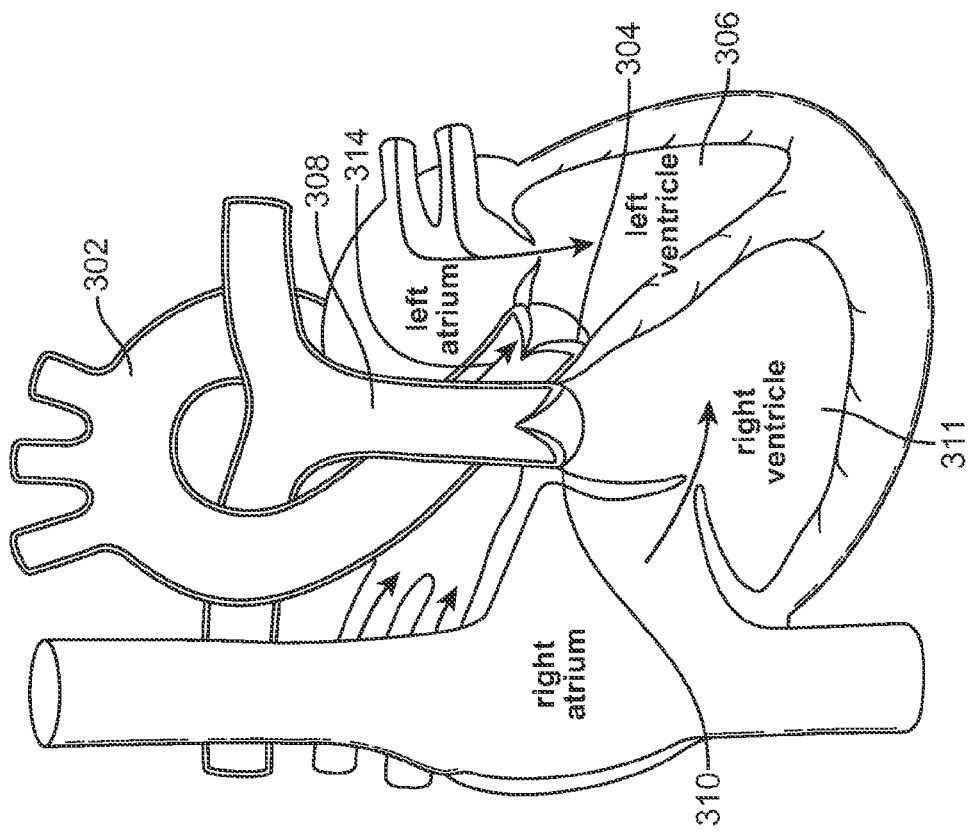
FIGS. 3A-3B are schematic representations of blood flow through a healthy aortic valve.
Figure 3B:
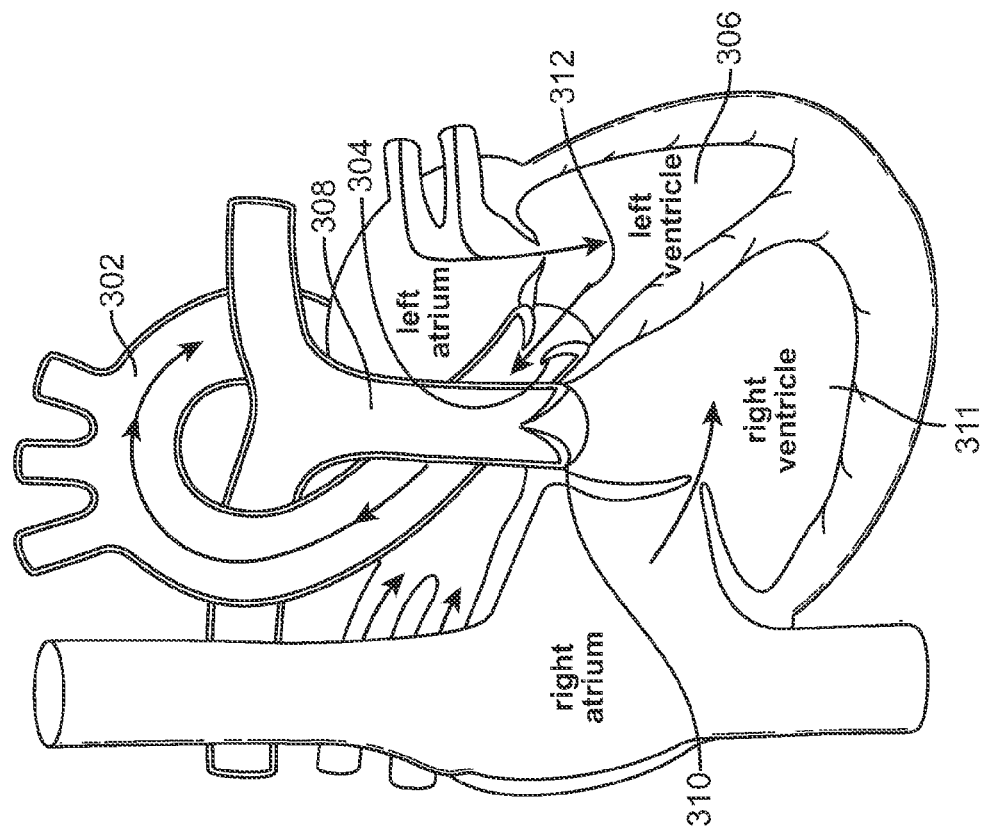
Figure 5:
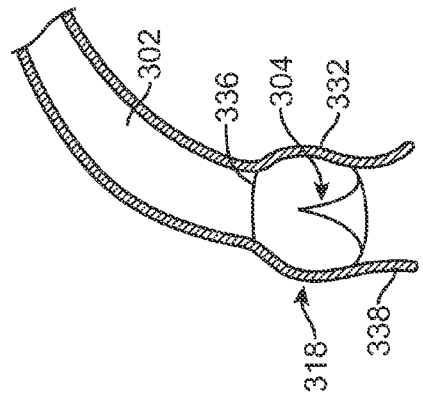
FIG. 5 is a cross-sectional illustration of the ascending aorta and the aortic valve.
Figure 6:
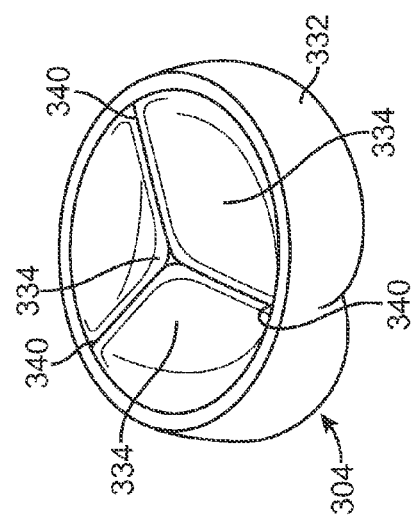
FIG. 6 is a schematic illustration of an aortic valve.
Figure 4:
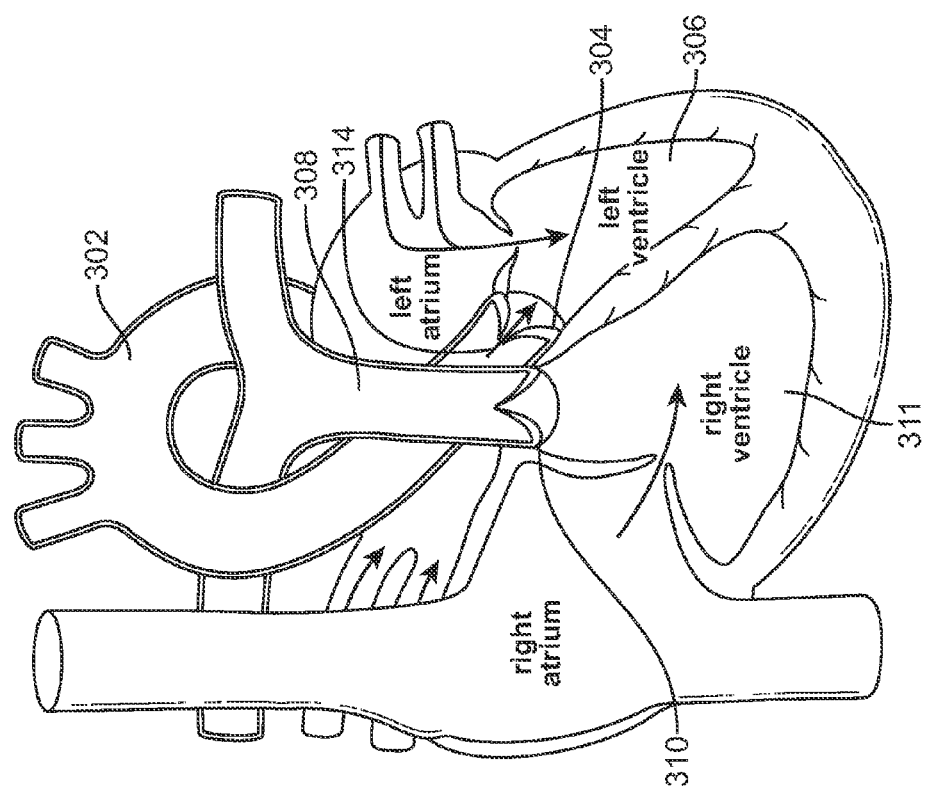
FIG. 4 is a schematic representation of blood flow through an incompetent aortic valve.
Figure 8B:
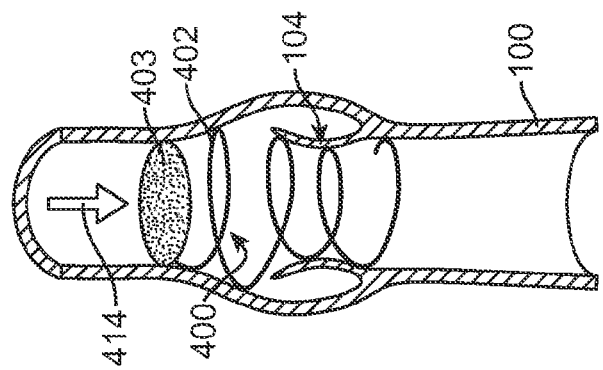
FIGS. 8A-8B are schematic representations of the one-way valve of FIG. 7 located in a vein at the location of a venous valve.
Figure 8A:
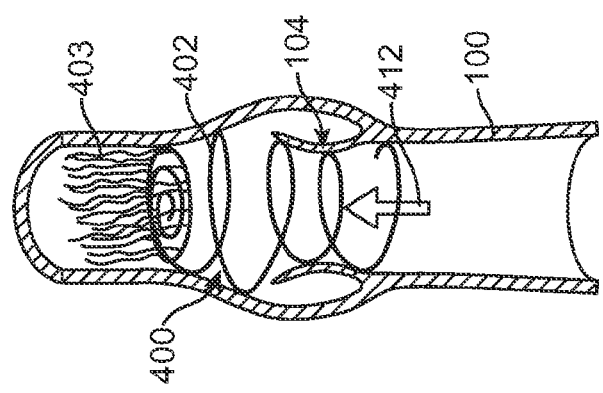
Figure 9B:
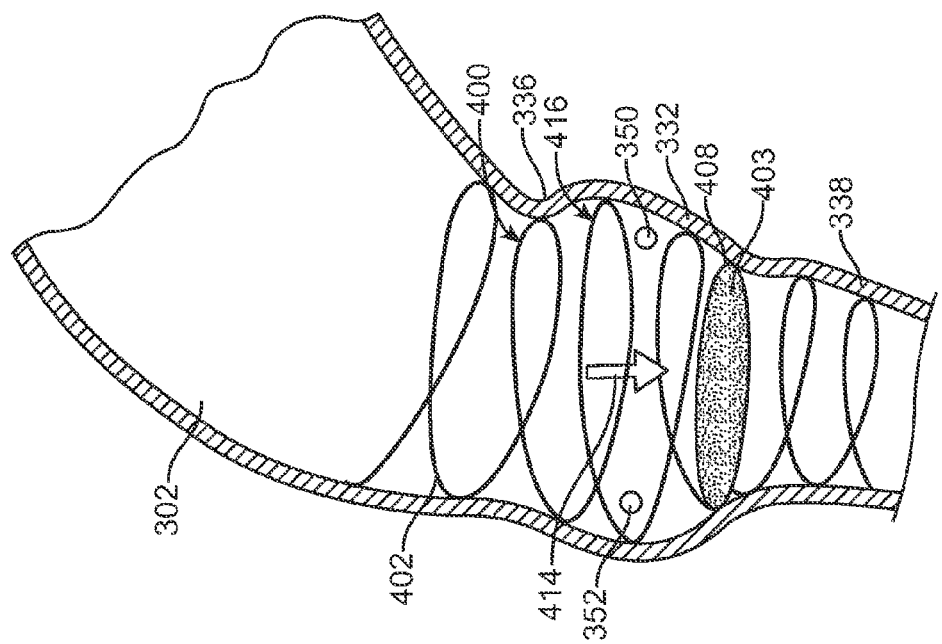
FIGS. 9A-9B are schematic representations of the one-way valve of FIG. 7 located at the aortic valve.
Figure 9A:
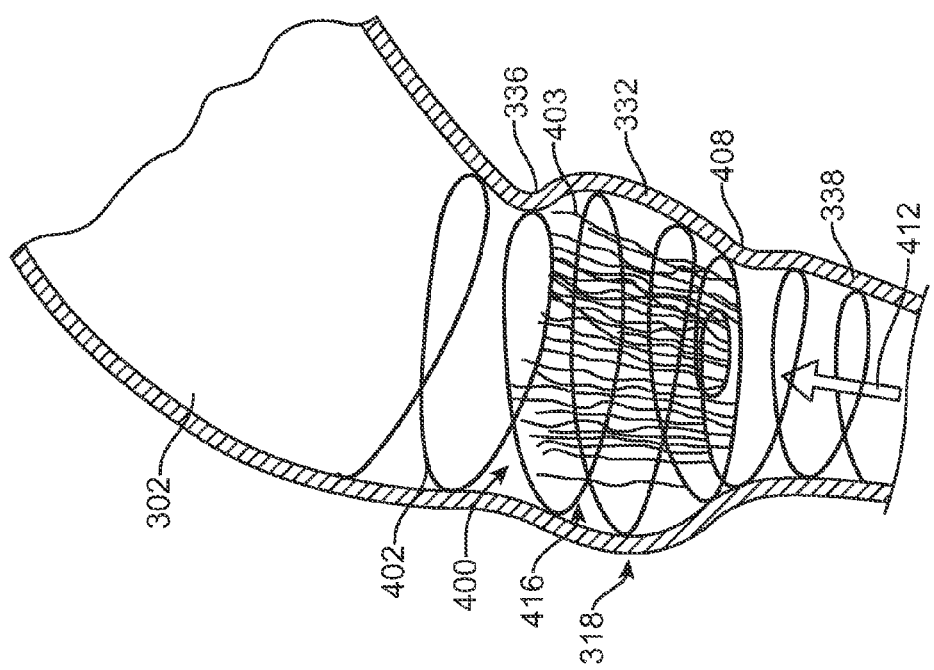

In the embodiment shown in FIG. 7, frame 402 is a wire formed into a tubular coil. In FIG. 7 (and FIGS. 8-16), the frame is shown in its expanded configuration. A portion of frame 402 includes a platform 408. As shown in FIG. 7, platform 408 is formed by the nitinol wire extending in a circular, or spiral, pattern towards a longitudinal axis 410 of frame 402. Filaments 403 are coupled to frame 402 at platform 408. When blood flows in the direction of arrow 412, filaments 403 extend in the direction of flow, as shown in FIGS. 8A and 9A. When there is a pressure drop such that blood does not flow in the direction of arrow 412, filaments 403 rest against platform 408, as shown in FIGS. 8B and 9B, to create a barrier to retrograde blood flood. Filaments 403 may be made of biocompatible, non-thrombotic materials such as, but not limited to, Polyethylene terephthalate (Dacron®) and expanded polytetrafluoroethylene (ePTFE).

FIGS. 8A-8B are schematic illustrations of valve 400 installed in a vein 100 at the location of a venous valve 104. FIGS. 8A-8B show frame 402 in its expanded configuration. Frame 402 is installed in vein 100 such that frame 402 holds venous valve 104 in an open configuration. FIG. 8A shows filaments 403 extended in the direction of blood flow shown by arrow 412, permitting blood to flow back towards the heart. FIG. 8B shows filaments 403 resting against platform 408 of frame 402 to prevent retrograde blood flow 414. When installed in a vein as shown in FIGS. 8A-8B, the length of filaments 403 is preferably 0.5 to 1.0 times the diameter of vein 100.

Figure 13B:
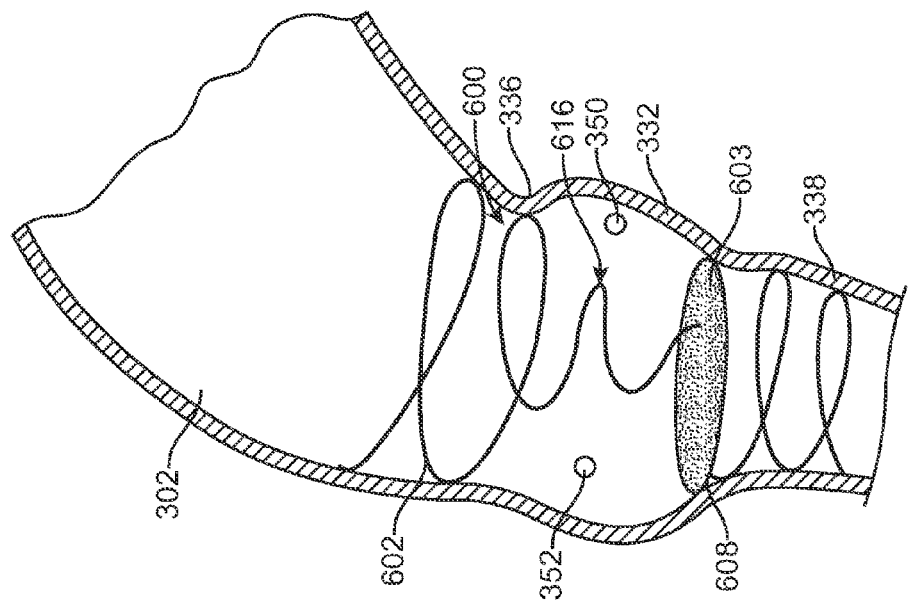
FIGS. 13A-13B are schematic representations of the one one-way valve of FIGS. 11A-11B located at the aortic valve.
Figure 13A:
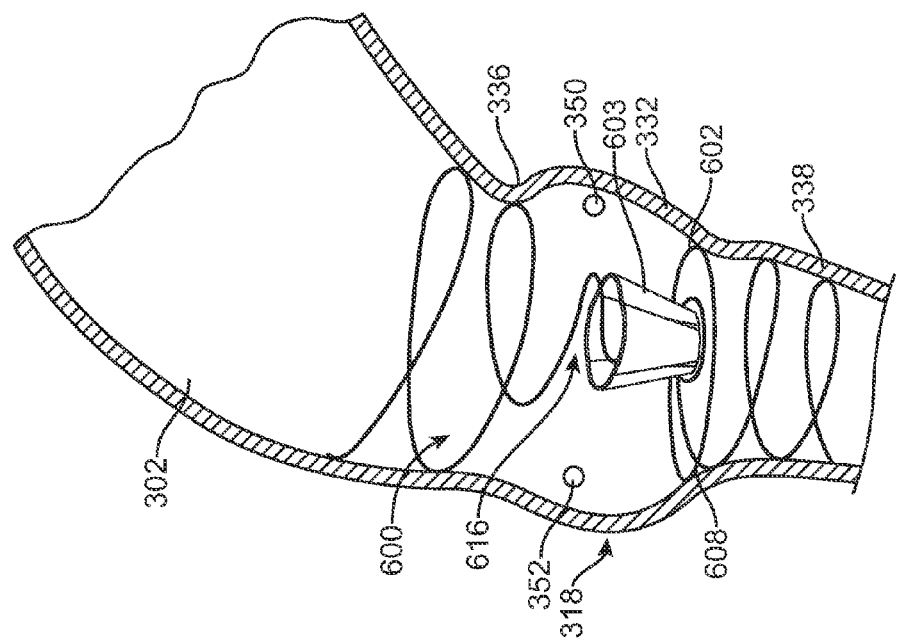

FIGS. 9A-9B are schematic illustrations are schematic illustrations of valve 400 installed at the aortic valve 304. In this embodiment frame 402 of valve 400 extends distally away from the heart beyond platform 408. This allows frame 402 to engage the sinotubular junction 336 and the aorta 302 to secure the frame in place. Frame 402 also extends to the annulus 338 to secure frame 402. In the embodiment shown in FIGS. 9A-9B, a middle portion 416 of frame 402 has a large diameter in its expanded configuration in order to engage the sinuses 318 and assist in maintaining sinotubular definition (i.e., the relationship between the diameters of the sinuses, the sinotubular junction, and the ascending aorta). However, middle portion 416 may alternatively have a reduced diameter, as shown in FIGS. 13A-13B. Further, valve 400 may be installed such that frame 402 holds aortic valve 304 in an open configuration (not shown but similar to venous valve embodiment of FIGS. 8A-8B) to effectively disable the aortic valve to prevent inefficiency of the aortic valve from disrupting natural blood flow.

During ventricular systole, pressure rises in the left ventricle. When the pressure in the left ventricle rises sufficiently, filaments 403 of valve 400 are forced to extend towards the aorta, thus allowing blood to flow in the direction of arrow 412. When ventricular systole ends, pressure in the left ventricle rapidly drops. Filaments 403 are flexible and light enough such that this drop in pressure causes filaments 403 to fall towards the left ventricle and getting caught against platform 408 to prevent retrograde blood flow 414.

As noted in the Background section above, a concern in aortic valve replacements is maintaining flow into the coronary ostia. As can be seen in FIGS. 9A-9B (and in FIGS. 13A-13B described below), the coil design of valve 400 will not risk blocking the coronary ostia 350, 352. Accordingly, valve 400 (as well as the other one-way valve embodiments described herein) provides an advantage over existing valve replacement devices that require openings to match the coronary ostia, or other accommodations to ensure that the coronary ostia are not blocked.

Figure 10A:
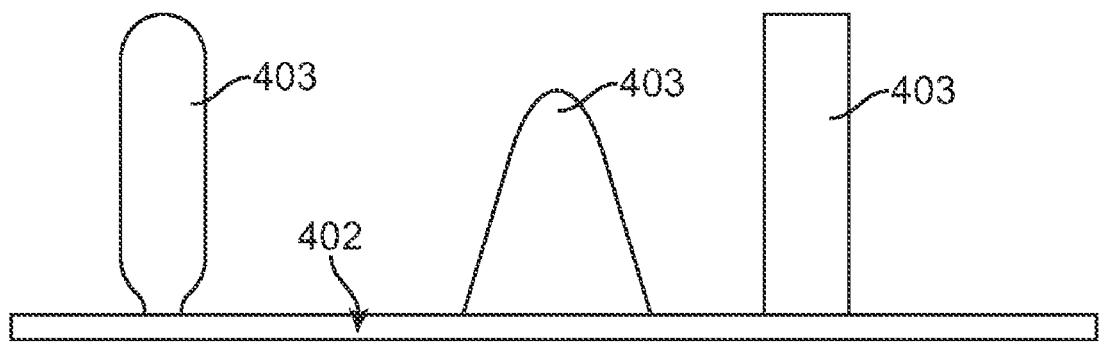
FIGS. 10A-10B are schematic representations of configurations of the filaments of the valve of FIG. 7.
Figure 10B:
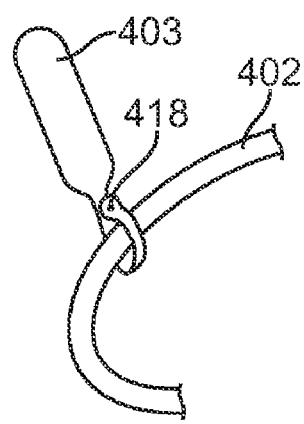

FIGS. 8A-8B and 9A-9B show filaments 403 as small thread-like strands. However, filaments 403 can be any shape, such as elliptical, triangular, and rectangular, as shown in FIG. 10A. Filaments 403 can be coupled to frame 402 by a thread, an adhesive, or any other means known to those skilled in the art. In the embodiment shown in FIG. 10B, a portion of each filament 403 is wrapped around the wire of frame 402 and a thread 418 attaches the filament 403 to itself.

Figure 11B:
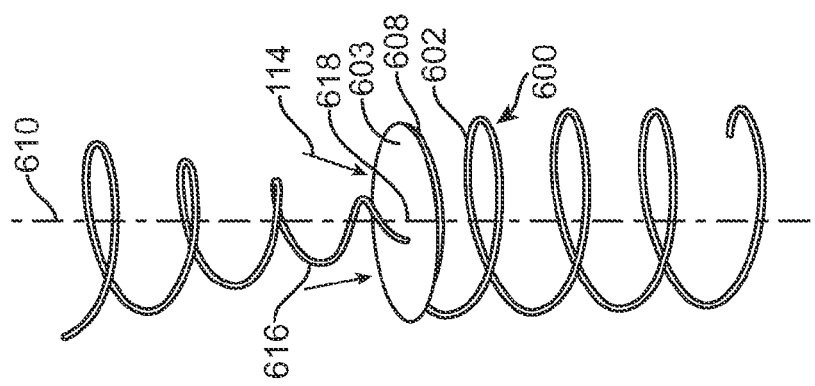
FIGS. 11A-11B are schematic representations of a one-way valve in accordance with another embodiment hereof.
Figure 11A:
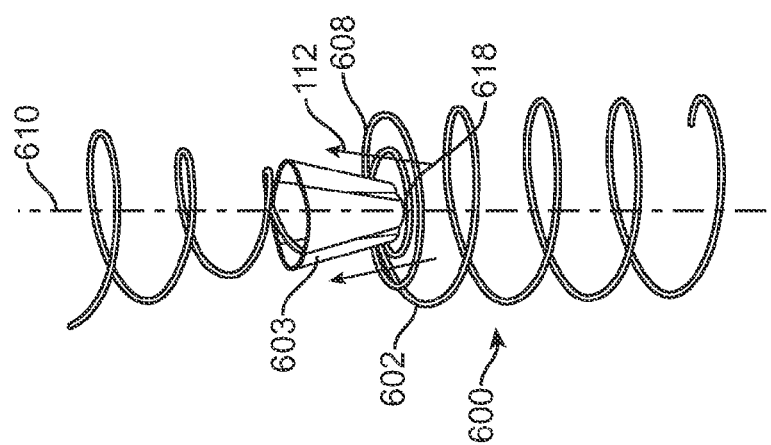

FIGS. 11A-11B are schematic representations of one-way valve 600 in accordance with another embodiment hereof. Valve 600 includes a coil or frame 602 and a flap 603 coupled to the frame 602. Frame 602 similar to frame 402 and is preferably formed from a shape memory material, such as a nickel-titanium alloy (Nitinol), such that frame 602 is self-expanding. It would be understood by those skilled in the art that frame 602 can be made of other materials used, for example, in stents, and may be balloon expandable. In the embodiment shown in FIGS. 11A-11B, frame 602 is a wire formed into a tubular coil. Flap 603 may be made from non-thrombotic materials such as Polyethylene terephthalate (Dacron®) and expanded polytetrafluoroethylene (ePTFE).

A portion of frame 602 includes a platform 608. As shown in FIG. 11A, platform 608 is formed by the nitinol wire extending in a circular pattern towards a longitudinal axis 610 of frame 602. Flap 603 is coupled to frame 602 at platform 608 by a thread 618. Thread 618 couples flap 603 to frame 602 generally near the center flap 603 to allow the periphery of flap 603 to move in response to forces generated where valve 600 is installed. In particular, when blood flows in the direction of arrow 112, the periphery of flap 603 folds or extends in the direction of flow, as shown in FIG. 11A. When there is a pressure drop such that a force is generated in the direction of arrow 114, flap 603 rests against platform 608, as shown in FIG. 11B, to create a barrier to retrograde blood flood. As best seen in FIG. 11B, a middle portion 616 of frame 602, adjacent to flap 603 in the blood flow direction, has a reduced diameter.

This reduced diameter allows flap 603 to fold without interference from frame 602. Flap 603 is generally circular in shape, although the shape of flap 603 can be modified to fit the particular location in which it is to be installed.

Figure 12B:
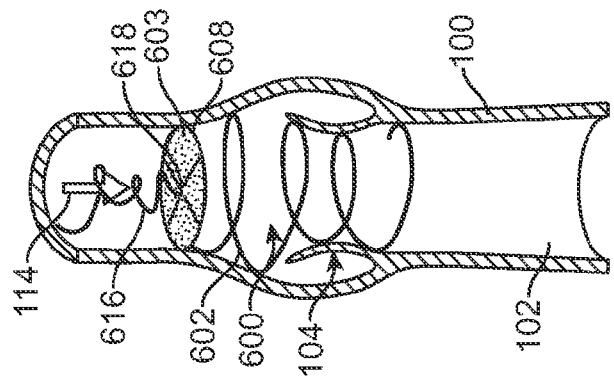
FIGS. 12A-12B are schematic representations of the one-way valve of FIGS. 11A-11B in a vein at the location of a venous valve.
Figure 12A:
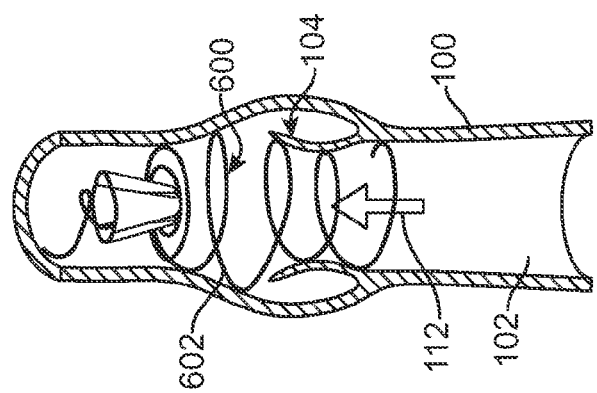

FIGS. 12A-12B are schematic illustrations of valve 600 installed in a vein 100 at the location of a venous valve 104. FIGS. 12A-12B show frame 602 in its expanded configuration. Frame 602 is installed in vein 100 such that frame 602 holds venous valve 104 in an open configuration. FIG. 12A shows flap 603 folded in the direction of blood flow shown by arrow 112, permitting blood to flow back towards the heart. FIG. 12B shows flap 603 resting flat against platform 608 of frame 602 to prevent retrograde blood flow 114.

FIGS. 13A-13B are schematic illustrations of valve 600 installed at the aortic valve 304. In this embodiment frame 602 of valve 600 extends distally away from the heart beyond platform 608. This allows frame 602 to engage the sinotubular junction 336 and the aorta 302 to secure frame 602 in place. Frame 602 also extends to the annulus 338 to secure frame 602. In the embodiment shown in FIGS. 13A-13B, middle portion 616 of frame 602 has reduced diameter in its expanded configuration in order to allow flap 603 to fold in the direction of blood flow. During ventricular systole, pressure rises in the left ventricle. When the pressure in the left ventricle rises sufficiently, flap 603 of valve 600 folds toward the aorta, thus allowing blood to flow in the direction of arrow 112. When ventricular systole ends, pressure in the left ventricle rapidly drops. Flap 603 is flexible and light enough such that this drop in pressure causes flap 603 to unfold towards the left ventricle until it rests against platform 608 to prevent retrograde blood flow 114.

Figure 14:
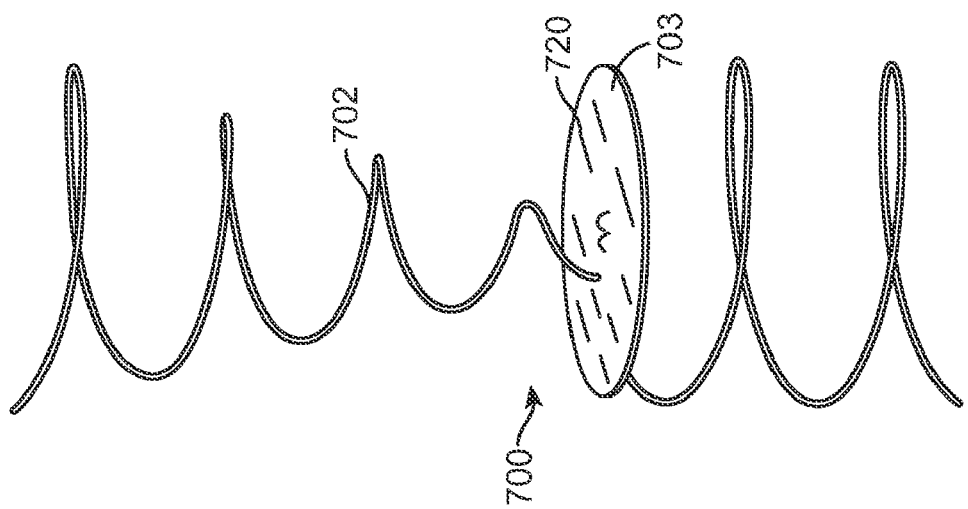
FIG. 14 is a schematic representation of a one-way valve in accordance with another embodiment hereof.

FIG. 14 is a schematic representation of a valve 700 in accordance with another embodiment hereof. Valve 700 is similar to valve 600 shown in FIGS. 11-13 in that it includes a frame 702 and a flap 703 coupled to frame 702. However, in the embodiment shown in FIG. 14, shape memory fibers or wires 720 are incorporated into flap 703. The shape memory fibers 720 can be, for example, nitinol fibers. Shape memory fibers 720 are incorporated into flap 703 such that shape memory fibers have a natural orientation that would orient flap 703 flat or generally perpendicular to the direction of blood flow. In other words, the natural orientation of shape memory fibers 720 would tend to keep flap 703 closed. However, this natural orientation would be overcome by the pressure of blood flow (upwards in FIG. 14) to open valve 700. When there is insufficient blood flow pressure to overcome the natural orientation of flap 703, flap 703 will close. This embodiment provides for a more definite closing of flap 703, rather than relying on retrograde blood flow to close the valve. The embodiment of FIG. 14 can be used in a vein or at the aortic valve, as shown in FIGS. 12 and 13 with respect to valve 600. The portions of valve 700 not particularly described are identical to those portions in FIGS. 11-13, or can be as described in other embodiments herein.

Figure 15B:
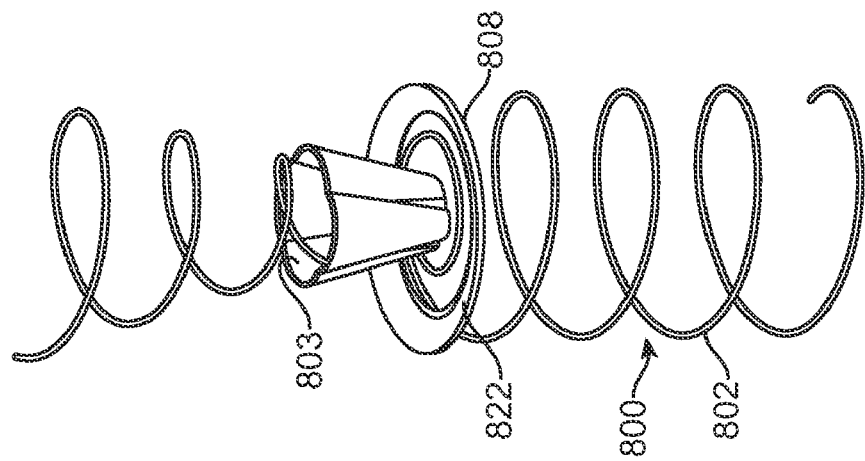
FIGS. 15A-15B are schematic representations of a one-way valve in accordance with another embodiment hereof.
Figure 15A:
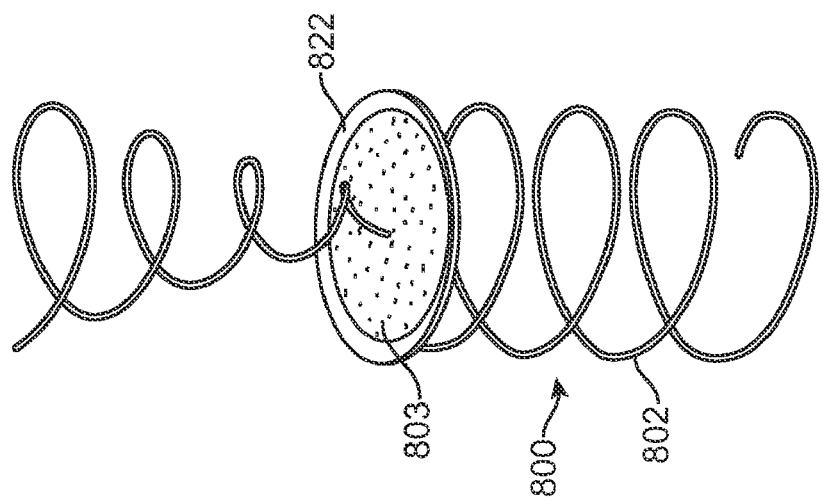

FIGS. 15A-15B are schematic representations of another embodiment of a one-way valve 800. Valve 800 is similar to valve 600 shown in FIGS. 11-13 in that it includes a frame 802 and a flap 803 coupled to frame 802. However, in the embodiment shown in FIGS. 15A-15B, a sealing ring 822 is coupled to the outer periphery of platform 808 of frame 802. Sealing ring may be made out of, but not limited to, silicone. As can be seen in FIG. 15A, when flap 803 is closed (i.e., resting against platform 808), sealing ring 822 forms an outer ring around flap 803. Preferably, there is some overlap between flap 803 and sealing ring 822. As can be seen in FIG. 15B, when flap 803 opens, sealing ring 822 remains in place since it is coupled to platform 808. Sealing ring 822 provides a more definite seal at the outer periphery of valve 800 where frame 802 meets the inner wall of a vein or the sinus, depending on where valve 800 is installed. The embodiment of FIGS. 15A-15B can be used in a vein or at the aortic valve, as shown in FIGS. 12 and 13 with respect to valve 600. The portions of valve 800 not particularly described are identical to those portions in FIGS. 11-13, or can be as described in other embodiments herein. For example, the shape memory fibers described with respect to valve 700 can be used in valve 800.

Figure 16A:
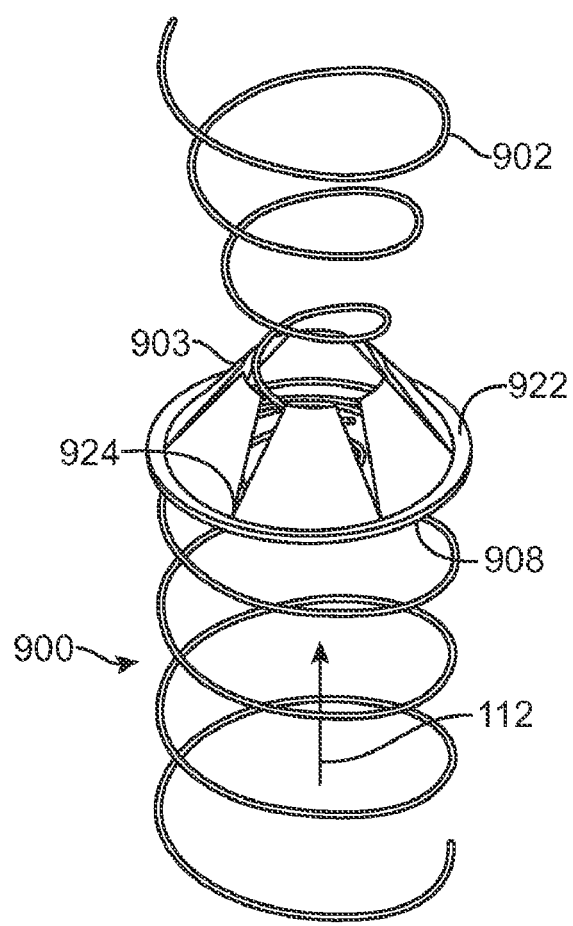
FIG. 16A-16B are schematic representations of a one-way valve in accordance with another embodiment hereof.
Figure 16B:
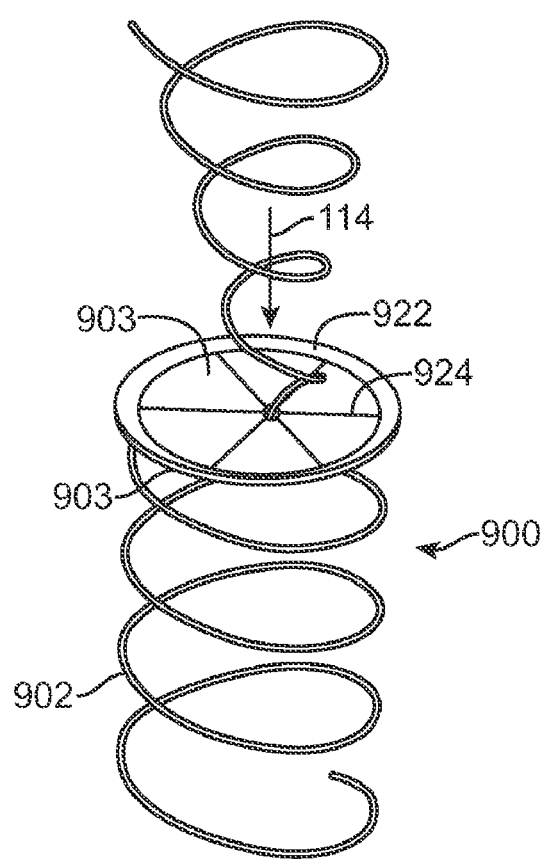

FIGS. 16A-16B are schematic representations of another embodiment of a one-way valve 900. Valve 900 is similar to valve 600 shown in FIGS. 11-13 and valve 800 shown in FIGS. 15A-15B in that it includes a frame 902 and a flap 903 coupled to frame 902. Further, valve 900 includes a sealing ring 922 similar to sealing ring 822 of FIGS. 15A-15B, although a sealing ring is not required. In the embodiment of FIGS. 16A-16B, flap 903 is coupled to platform 908 at the periphery of flap 903. Flap 903 also includes slits or cuts 924 extending from a center of flap 903 to the outer peripheral portion of flap 903. The slits 924 preferably do not extend all the way through the outer edge of flap 902, such that flap 903 is a single piece with slits 924, rather than several smaller pieces. In the embodiment shown in FIGS. 16A-16B, flap 903 includes six slits 924 such that there are six portions of flap 903. Flap 903 may be attached directly to the outer periphery of platform 908 by threading, adhesive, or other methods known to those skilled in the art. Alternatively, the outer periphery of flap 903 may be attached directly to sealing ring 922. Due the structure of this embodiment, when pressure from blood flow is in the direction of arrow 112, as shown in FIG. 16A, flap 903 opens from the center and the six portions extend in the direction of the blood flow. When there is a drop in pressure, flap 903 closes to prevent retrograde blood flow in the direction of arrow 114, as shown in FIG. 16B. The embodiment of FIGS. 16A-16B can be used in a vein or at the aortic valve, as shown in FIGS. 12 and 13 with respect to valve 600. The portions of valve 900 not particularly described are identical to those portions in FIGS. 11-13, or can be as described in other embodiments herein.

Figure 17:
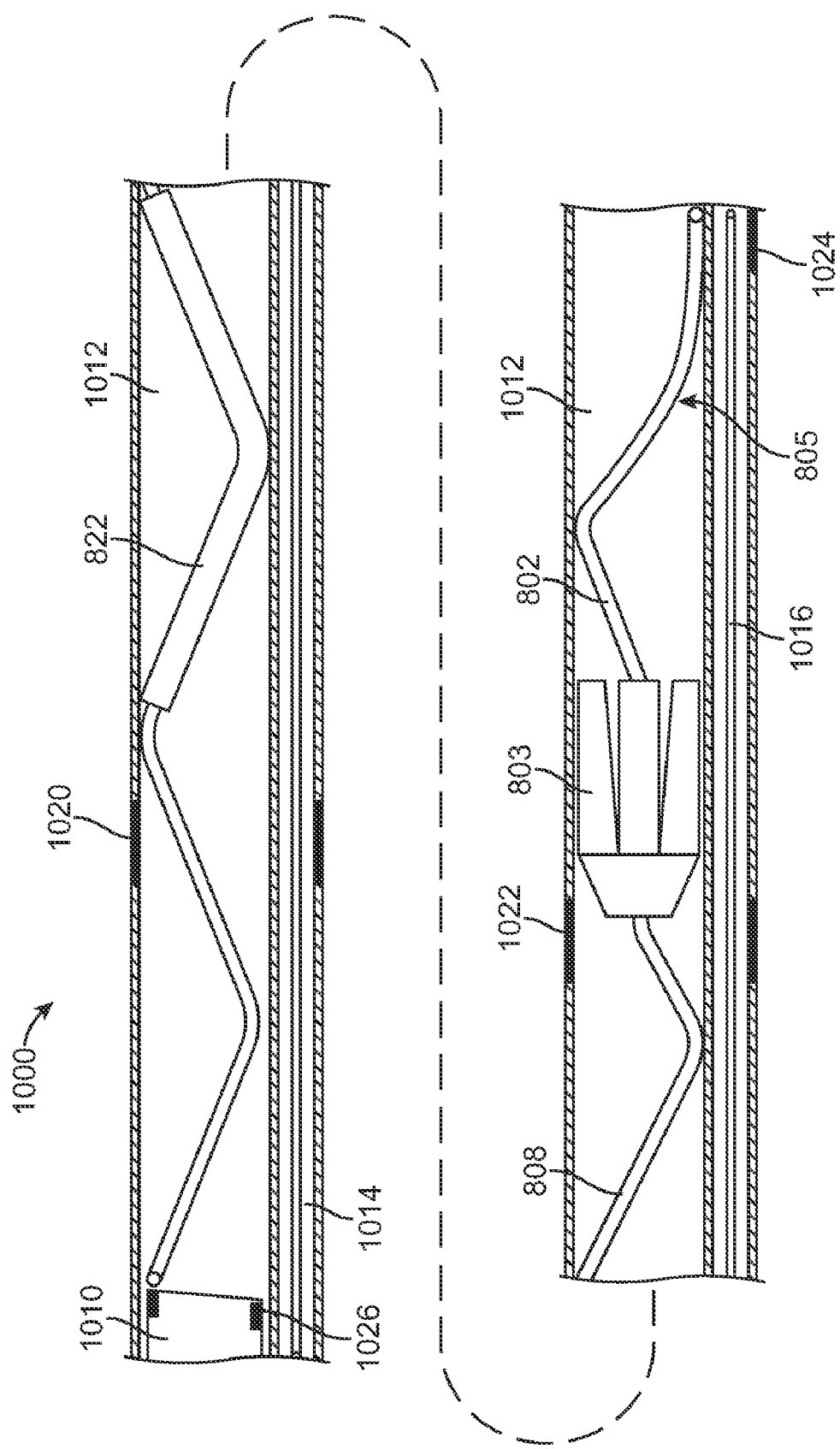
FIG. 17 is a schematic representation of a delivery catheter for a one-way valve.

FIG. 17 is a schematic illustration of a delivery catheter 1000 for delivering a one-way valve of the present disclosure. Delivery catheter 1000 includes lumen 1012 for holding the one-way valve. In the embodiment shown in FIG. 17, valve 800 described above with respect to FIGS. 15A-15B is illustrated. It would be understood by those skilled in the art that any of the valves described herein could be delivered in delivery catheter 1000. Delivery catheter 1000 also includes a guidewire lumen 1014 through which a guidewire 1016 can pass. Delivery catheter further includes a pusher 1010 disposed at a proximal end of valve 800. As illustrated in FIG. 17, frame 802 of valve 800 is unwound or straightened to fit in lumen 1012. This illustrates the compressed configuration of the frame for delivery to the target site. This straightened configuration permits the valve to fit into a smaller diameter delivery catheter than other replacement valves. For example, delivery catheter 1000 may be in the range of 0.075 to 0.130 inches in diameter, compared to existing technologies which are in the range of 0.235 to 0.315 inches in diameter. Due to its shape memory material, frame 802 will revert to its coiled, tubular configuration when released from catheter 1000.

Figure 18:
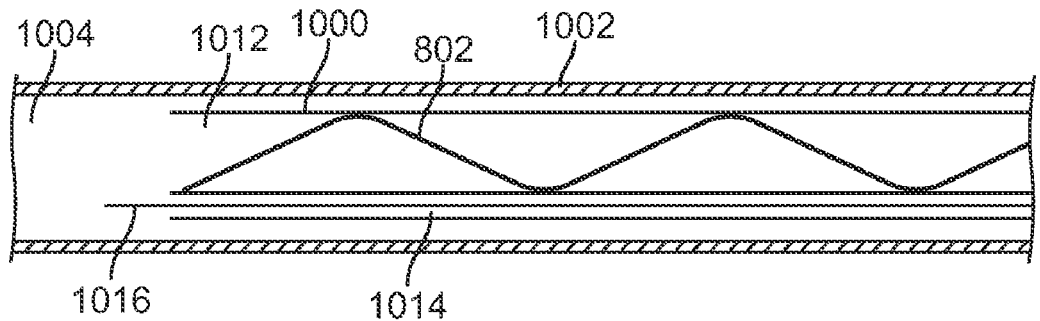
FIGS. 18-20 are schematic representations of a method a delivering a one-way valve to replace an incompetent valve.
Figure 19:
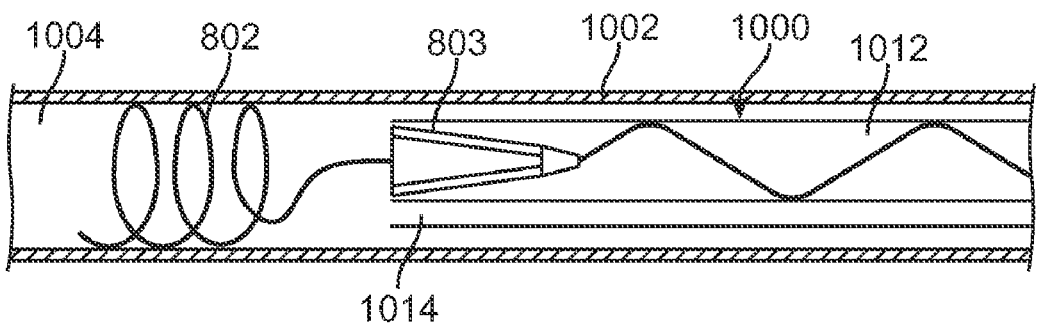
Figure 20:
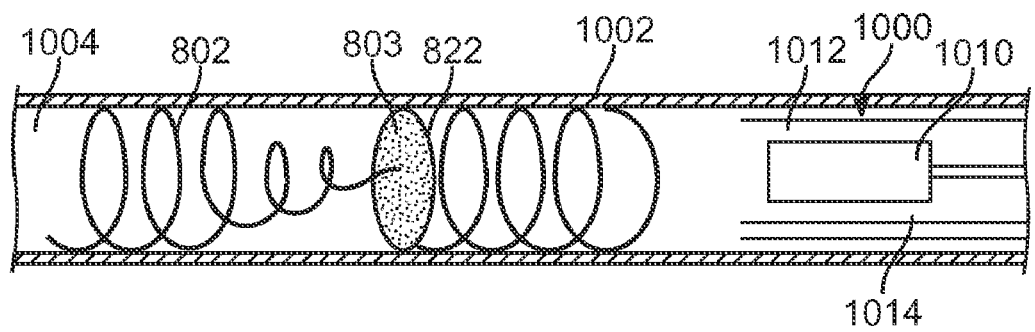

FIGS. 18-20 illustrate schematically a method of delivering valve 800 to the location of an incompetent venous valve using delivery catheter 1000. Initially luminal access to a desired peripheral vein 1002, such as the greater or lesser saphenous, femoral, or popliteal veins, is obtained using standard percutaneous techniques. Guidewire 1016 is then maneuvered through the vasculature to rest across a target location within lumen 1004 of vein 1002 where valve 800 is to be inserted. Guidewire 1016 is then backloaded into guidewire lumen 1014 of catheter 1000, and catheter 1000 is advanced over guidewire 1016 to the target location, as shown in FIG. 18.

Once catheter 1000 is in position, guidewire 1016 can be removed. Pusher 1010, shown in FIG. 17 may either be advanced distally, or catheter 1000 may be withdrawn proximally as pusher 1010 remains in place, or a combination of the both, in order to achieve relative longitudinal movement between pusher 1010 and catheter 1000. Due to this relative longitudinal movement, valve 800 begins exiting catheter 1000, as shown in FIG. 19. As frame 802 of valve 800 exits catheter 1000, frame 802 reverts to its coiled configuration, as shown in FIG. 19. Continued relative longitudinal movement between catheter 1000 and pusher 1010 results in the valve 800 completely exiting catheter 1000 and frame 802 securing valve 800 against 1002. One skilled in the art would recognize that valve 800 can be loaded into catheter 1000 with either end of frame 802 facing distally, depending on the access point, valve location, and blood flow direction of the vein being accessed. Further, one skilled in the art would recognize that other delivery catheters and methods may be used to deliver a valve to a desired location. For example, a tubular, non-coiled self expanding frame could be utilized for the valve, and conventional means to deliver a tubular, non-coiled, self-expanding stent could be utilized.

During delivery, catheter 1000 and/or valve 800 need to be visualized in order to ensure proper placement. Visualization of valve 800 may be accomplished, for example, by making frame 802 using a Nitinol wire with a tantalum core, as discussed above. In another example, marker bands, made from tantalum, gold, platinum, or other similar materials, may be added to frame 802 at various locations, as would be known by those of ordinary skill in the art. For example, marker bands may be added to the proximal and distal ends of frame 802. In another example, pusher 1010 may be made of a radiopaque material or may have marker bands 1026 added thereto, as shown in FIG. 17. Further, catheter 1000 may have marker bands along the length thereof, for example, marker bands 1020, 1022, and 1024 shown in FIG. 17. When marker band 1026 of pusher 1010 is aligned with one of the marker bands of catheter 1000, the user knows that a certain portion of the valve 800 has exited catheter 1000 and is deployed. For example, as shown in FIG. 17 but not to scale, when marker band 1026 of pusher 1010 is aligned with marker band 1020 of catheter 1000, valve flap 803 has been deployed. Similarly, when marker band 1026 of pusher 1010 is aligned with marker band 1022 of catheter 1000, platform 808 has been deployed, and when marker band 1026 is aligned with marker band 1024, all of frame 802 of valve 800 has exited catheter 1000 and deployed. Although three marker bands for catheter 1000 have been described in this embodiment, it would be understood that more or less marker bands may be used. Further, other methods of visualizing valve 800 and catheter 1000 would be apparent to those of ordinary skill in the art.

The valves and delivery catheter described herein would also permit partial deployment of the valve in order to verify its function, and possible retraction and repositioning of the valve, if necessary. Accordingly, the distal portion 805 of frame 802, flap 803, and platform 808 can be deployed. The operator can then visualize valve function. Distal portion 805 would allow for temporary anchoring to verify valve function. If the valve needs to be repositioned or otherwise recovered, a hook or grasping mechanism (not shown) on the pusher could retract the valve back into the delivery catheter.

The proximal portion of the valve could also include a hook or other capturing mechanism such that the entire valve could be deployed and then recaptured either for repositioning, or if the device needed removal for an unforeseen reason.

It would be understood by those skilled in the art that although FIGS. 18-20 were described with respect to delivery of a replacement venous valve, delivery catheter 1000 of FIG. 17, and the method illustrated in FIGS. 18-20 can also be utilized to deliver a valve to replace an aortic valve or pulmonary valve.

While various embodiments hereof have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope hereof should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A one-way artificial valve comprising:
    a frame formed of a continuous wire, wherein said wire forms into a tubular coil, said frame having a radially compressed configuration and a radially expanded configuration, wherein in the radially expanded configuration the frame includes a platform and a longitudinal axis; and
    a flap coupled to the frame, wherein the flap includes a plurality of slits disposed in the flap, wherein the flap is generally circular in shape when resting against the platform, wherein the flap is generally coupled to the frame at an outer periphery of the flap, and wherein the slits allow a center portion of the flap to fold generally in a first direction in response to a force in the first direction and wherein in absence of the force the first direction the flap rests against the platform blocking flow in a second direction opposite the first direction.

2. The valve of claim 1, wherein the frame is generally tubular in its expanded configuration.

3. The valve of claim 2, wherein the frame comprises a wire made of a shape memory material.

4. The valve of claim 3, wherein the shape memory material is a nickel-titanium alloy.

5. The valve of claim 1, wherein the flap is made of a material selected from polyethylene terephthalate and expanded polytetrafluoroethylene.

6. The valve of claim 1, further comprising a sealing ring disposed about the periphery of the platform and extending radially inwardly towards the longitudinal axis of the frame, wherein the outer periphery of the flap overlaps an inner periphery of the sealing ring.

7. The valve of claim 6, wherein the sealing ring is made of silicone.

8. The valve of claim 1, wherein the flap is coupled to the frame by a thread.

9. The valve of claim 1, wherein the flap includes a plurality of shape memory fibers disposed therein, wherein the shape memory fibers are naturally oriented to cause the flap to return to a generally flat, generally circular shape.

10. A one-way artificial valve comprising:
    a frame formed from a continuous wire, the frame having a radially compressed and a radially expanded configuration wherein the wire forms a tubular coil, wherein in the radially expanded configuration a portion of the wire extends in a spiral toward around a longitudinal axis of the coil to form a platform; and a flap coupled to the frame at the platform, wherein the flap is configured such that a force in a first direction causes the flap to fold generally in the first direction and wherein in absence of the force the first direction the flap rests against the platform blocking flow in a second direction opposite the first direction.

11. The valve of claim 10, wherein the flap is generally circular in shape when resting against the platform, and wherein the flap is coupled to the frame generally at the center of the flap.

12. The valve of claim 10, wherein in the radially compressed configuration the wire is substantially elongated.

13. The valve of claim 10, wherein the continuous wire is a shape memory material.

14. The valve of claim 13, wherein the shape memory material is a nickel-titanium alloy.

15. The valve of claim 10, wherein the flap is made of a material selected from polyethylene terephthalate and expanded polytetrafluoroethylene.

16. The valve of claim 10, further comprising a sealing ring disposed about the periphery of the platform and extending radially inwardly towards the longitudinal axis of the frame, wherein an outer periphery of the flap overlaps an inner periphery of the sealing ring.

17. The valve of claim 16, wherein the sealing ring is made of silicone.

18. The valve of claim 10, wherein the flap is coupled to the frame by a thread.

19. The valve of claim 10, further comprising a plurality of slits disposed in the flap, wherein the flap is generally circular in shape when resting against the platform, wherein the flap is generally coupled to the frame at an outer periphery of the flap, and wherein the slits allow a center portion of the flap to fold generally in the first direction in response to the force.

20. The valve of claim 10, wherein the flap includes a plurality of shape memory fibers disposed therein, wherein the shape memory fibers are naturally oriented to cause the flap to return to a generally flat, generally circular shape.

21. A one-way artificial valve comprising:

a frame formed having a radially compressed configuration and a radially expanded configuration wherein a wire forms a tubular coil, wherein in the radially expanded configuration the frame includes a platform and a longitudinal axis;

a flap coupled to the frame, wherein the flap is configured such that a force in a first direction causes the flap to fold generally in the first direction and wherein in absence of the force the first direction the flap rests against the platform blocking flow in a second direction opposite the first direction; and a sealing ring coupled to an outer periphery of the platform and extending radially inwardly from the outer periphery of the platform towards the longitudinal axis, an outer periphery of the flap overlapping with an inner periphery of the sealing ring when the flap rests against the platform.

22. The valve of claim 21, wherein the frame is formed from a continued wire made of a shape memory material, wherein in the radially compressed configuration the wire is substantially elongated.

23. The valve of claim 22, wherein the shape memory material is a nickel-titanium alloy.

24. The valve of claim 21, wherein the flap is made of a material selected from polyethylene terephthalate and expanded polytetrafluoroethylene.

25. The valve of claim 21, wherein the sealing ring is made of silicone.

26. The valve of claim 21, wherein the flap is coupled to the frame by a thread.

27. The valve of claim 21, wherein the flap includes a plurality of shape memory fibers disposed therein, wherein the shape memory fibers are naturally oriented to cause the flap to return to a generally flat, generally circular shape.

28. The valve of claim 21, further comprising a plurality of slits disposed in the flap, wherein the flap is generally circular in shape when resting against the platform, wherein the flap is generally coupled to the frame at the outer periphery of the flap, and wherein the slits allow a center portion of the flap to fold generally in the first direction in response to the force.

* * * * *